United States Patent
Heuft et al.

(10) Patent No.: US 6,338,272 B1
(45) Date of Patent: Jan. 15, 2002

(54) METHOD FOR DETERMINING PARAMETERS, FOR EXAMPLE LEVEL, PRESSURE, GAS COMPOSITION IN CLOSED CONTAINERS

(75) Inventors: Bernhard Heuft, Burgbrohl; Hans-Ulrich Goller, Bonn-Bad Godesberg, both of (DE)

(73) Assignee: Heuft Systemtechnik GmbH, Burgbrohl (DE)

( * ) Notice: Subject to any disclaimer, the term of this patent is extended or adjusted under 35 U.S.C. 154(b) by 0 days.

(21) Appl. No.: 09/297,915

(22) PCT Filed: Nov. 12, 1997

(86) PCT No.: PCT/EP97/06298

§ 371 Date: May 7, 1999

§ 102(e) Date: May 7, 1999

(87) PCT Pub. No.: WO98/21557

PCT Pub. Date: May 22, 1998

(30) Foreign Application Priority Data

Nov. 12, 1996 (DE) .......................................... 196 46 685

(51) Int. Cl.$^7$ ................................................ G01M 3/24
(52) U.S. Cl. ...................................... 73/290 V; 73/579
(58) Field of Search ................................ 73/290 V, 52, 73/570, 579, 574; 310/328

(56) References Cited

U.S. PATENT DOCUMENTS

| | | | |
|---|---|---|---|
| 3,802,252 A | 4/1974 | Hayward et al. ............... 73/52 |
| 4,535,627 A | 8/1985 | Prost et al. ............... 73/290 B |
| 4,536,887 A | * 8/1985 | Kaneda et al. ................ 381/92 |
| 4,580,448 A | * 4/1986 | Skrgatic ................... 73/290 V |
| 4,596,133 A | 6/1986 | Smalling et al. ........... 73/24.01 |
| 4,811,595 A | 3/1989 | Marciniak et al. ............ 73/149 |
| 4,896,535 A | * 1/1990 | Duckart et al. ........... 73/290 V |
| 4,991,433 A | 2/1991 | Warnaka et al. .......... 73/290 V |
| 5,144,838 A | 9/1992 | Tsuboi .......................... 73/579 |
| 5,353,631 A | 10/1994 | Woringer et al. ............... 73/52 |
| 5,585,567 A | * 12/1996 | Van Manen .................. 73/702 |
| 5,608,164 A | * 3/1997 | MacLauchlan ............... 73/599 |
| 5,819,818 A | * 10/1998 | Frawley ....................... 141/95 |
| 5,869,747 A | * 2/1999 | Hulsman ........................ 73/52 |

FOREIGN PATENT DOCUMENTS

| | | | | |
|---|---|---|---|---|
| DE | 32 10 302 A1 | * | 9/1983 | ........... G01L/11/00 |
| DE | 40 04 965 A1 | * | 8/1991 | ............. G01F/3/40 |
| EP | 0681168 A2 | | 11/1995 | ........... G01L/11/04 |
| GB | 2293450 A | | 3/1996 | ........... G01L/11/04 |
| JP | 3-89132 A | | 7/1991 | ............. G01M/3/24 |

* cited by examiner

Primary Examiner—Hezron Williams
Assistant Examiner—Rose M. Miller
(74) Attorney, Agent, or Firm—Gardner, Carton & Douglas

(57) ABSTRACT

In order to determine parameters of closed containers, primary mechanical oscillations are excited in a container wall. The secondary oscillations which are excited in the container by the primary mechanical oscillations of the container wall and which occur within the space between a closure and the liquid are picked up and analyzed, the parameters being determined from the ascertained frequency characteristic of these oscillations. In addition, the primary oscillations of the closure can also be picked up and analyzed, the internal pressure prevailing in the container being determined from the frequency of these primary oscillations. The frequencies of the primary and secondary oscillations can be determined by analysis of the frequency spectrum. The secondary oscillations can be picked up separately from the primary oscillations in that only those oscillations are picked up which occur within a time measurement window within which the primary oscillations have already decayed.

10 Claims, 3 Drawing Sheets

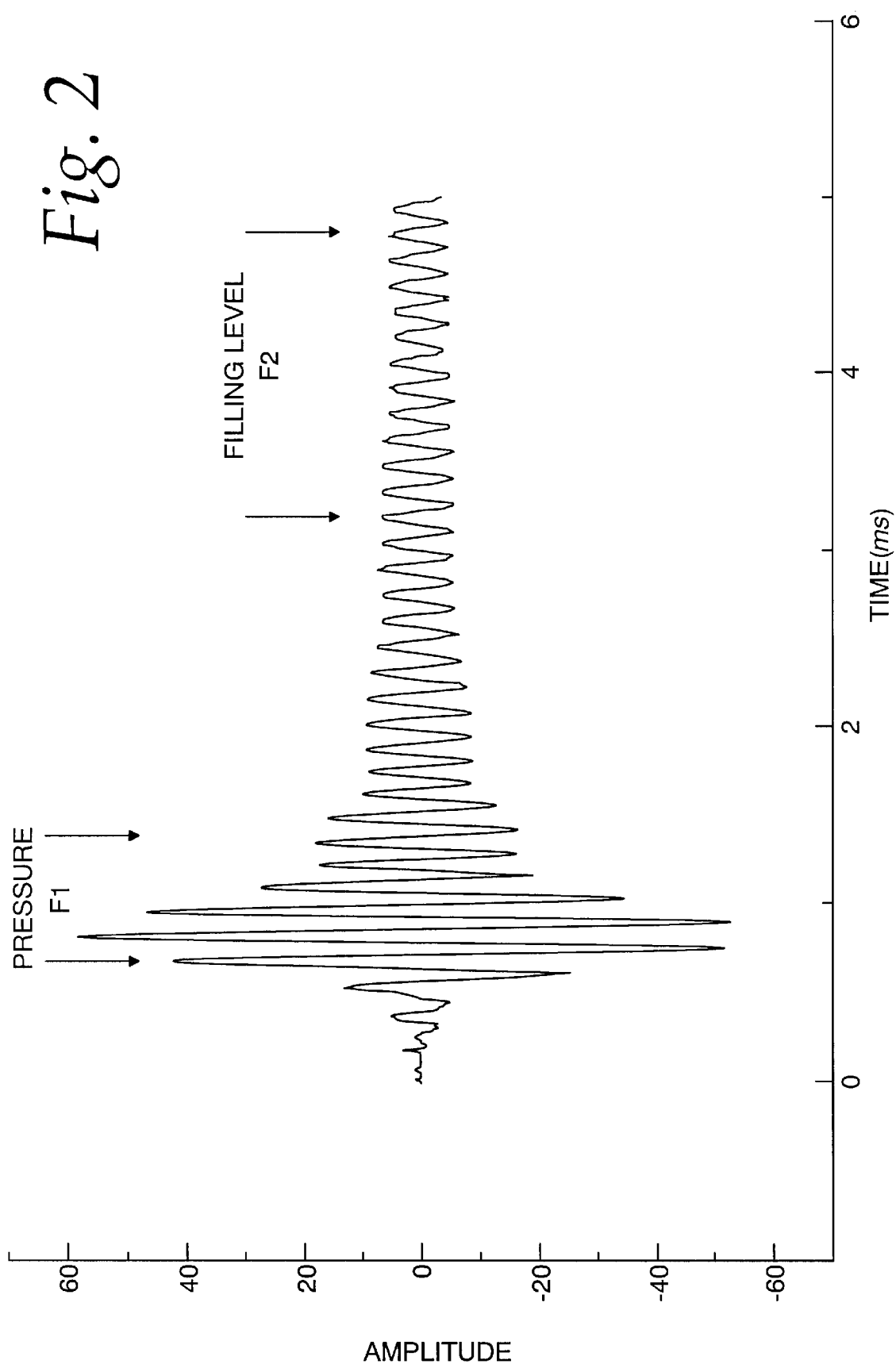

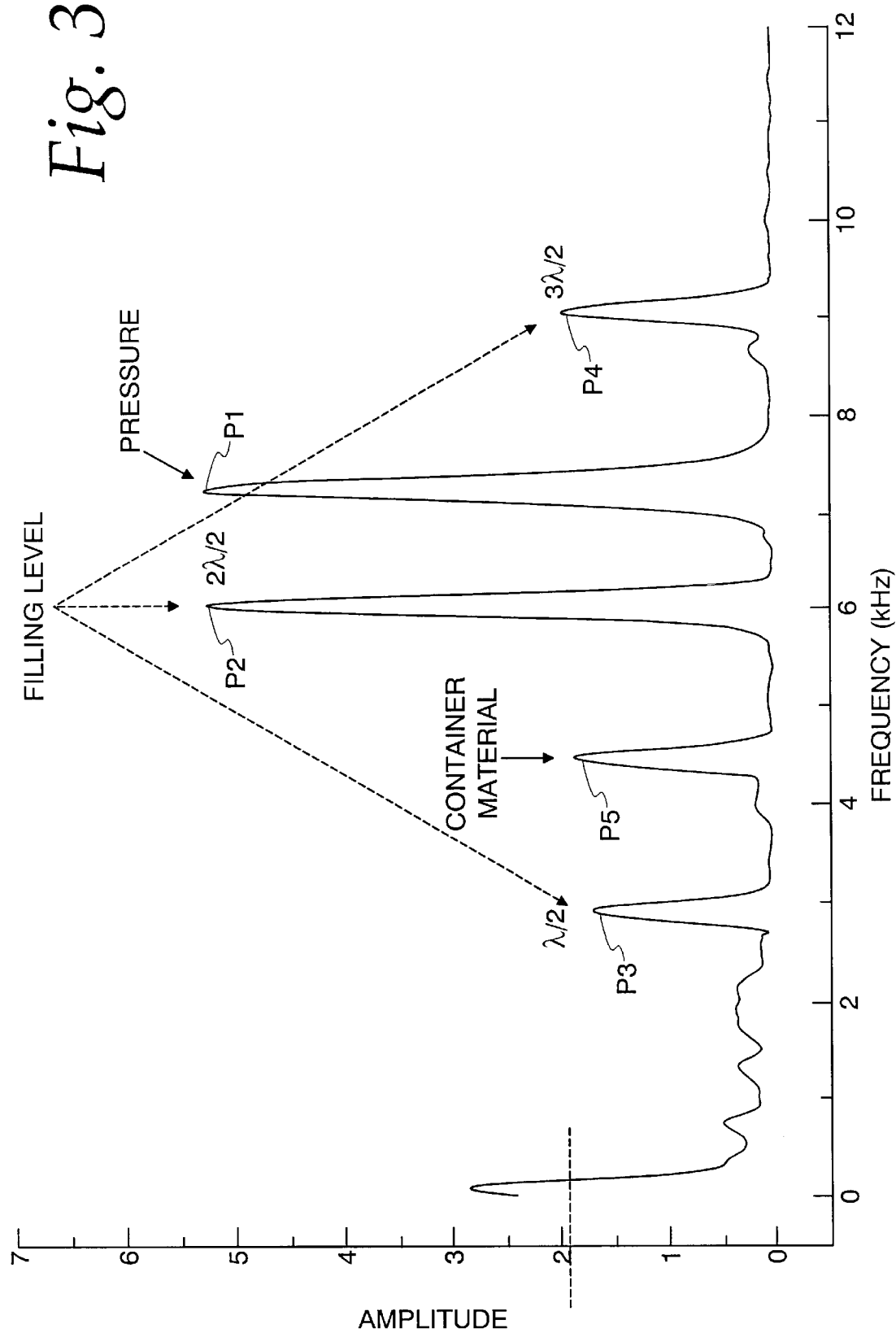

METHOD FOR DETERMINING PARAMETERS, FOR EXAMPLE LEVEL, PRESSURE, GAS COMPOSITION IN CLOSED CONTAINERS

BACKGROUND OF THE INVENTION

The invention concerns a method for the determination of parameters, e.g. filling level, pressure, gas composition in the head space and material condition, in closed containers, wherein a container wall is excited to produce mechanical oscillations and the resultant oscillations are picked up and analysed in respect of their chronological sequence or their frequency spectrum.

The filling level of liquids in containers is normally determined optically by means of light barriers, by checking of the weight of the container or by measurement of a high-frequency electromagnetic radiation absorbed by a container.

Methods are known for testing containers for leakages and for ascertaining the internal pressure, in which the cap of a container is displaced electromagnetically (U.S. Pat. No. 1,956,301). Furthermore, it is known that inferences on container states can be drawn not only from the displacement but also from the vibration frequency of the container walls (U.S. Pat. No. 2,320,390). Initially, the displacement and the vibrations of the container walls were measured mechanically. Since these vibrations result in acoustic signals, electronic circuits such as microphone arrangements (U.S. Pat. No. 3,290,922) or electrostatic sensors (U.S. Pat. No. 3,441,132) can also be used for this purpose.

It is further known that only sub-ranges of the signal spectrum are relevant to the checking of tightness or pressure, so that the electronic measures can be reduced to the evaluation of specific frequency ranges (U.S. Pat. No. 3,802,252). It thus became possible to digitise the filtered oscillation signal and, for the purpose of checking pressure, to count the number of periods during a measurement interval (U.S. Pat. No. 4,187,718). In order to enable the correct frequency of the cap oscillation to be measured constantly over a longer period, measures were taken by which the vibration signal was fed back to the exciter arrangement to achieve an undamped cap oscillation through repeated excitation with the cap frequency (U.S. Pat. No. 4,406,157). Furthermore, instead of concentrating on one frequency range in the evaluation of the vibration signal, it is possible to analyse the entire signal with the use of signal processors. Initially, the spectrum alone was examined for the presence of particular frequencies for the purpose of thereby detecting the presence of absence of defects (U.S. Pat. No. 5,144,838). It subsequently became possible to compare the measured frequency spectrum with stored reference spectra of containers with a known pressure in order to permit determination of a pressure value for the current container (U.S. Pat. No. 5,353,631).

The object of the invention is to create a method for the comprehensive quality testing of containers which can be performed with a particularly small amount of apparatus and provides very accurate results.

BRIEF SUMMARY OF THE INVENTION

This object is achieved according to the invention with a method of the type initially referred to, wherein the secondary oscillations which are excited by the primary mechanical oscillations of the cap and which are produced in the container within the excited container wall are picked up and analysed.

If a face of a container, e.g. the cap of a beverage container, is briefly raised with an electromagnetic pulse and then released, it is excited to produce a free, primary oscillation. The frequency of this oscillation is a measure of the cap tension which is determined by, amongst other factors, the pressure prevailing in the container. As the tension of a drum-head determines the sound of the drum, the lid oscillation varies in dependence on the internal pressure of the container. This primary oscillation of the cap is highly damped, so that the oscillation determined by the internal pressure decays rapidly. The short oscillation period is however sufficient to emit an acoustic signal into both the air space outside the container and the container volume itself. If this signal is picked up by means of a vibration pick-up, e.g. a microphone arrangement, this primary oscillation frequency can be ascertained in a first time measurement window by means of a relatively simple circuit through measurement of the duration of an oscillation period. The position and the length of the measurement window can be individually adapted to each container type. In the case of crown cap closures, for example, it can be said that this first time measurement window commences approximately 0.3 ms after the excitation of the cap oscillation and lasts for approximately 0.4 ms.

In order to obtain a sufficient number of primary oscillation amplitudes for the excitation of secondary oscillations, the method according to the invention is used primarily for containers which have at least one rigid container wall, e.g. a metal crown cap closure. Containers which are made from plastic or which have plastic closures are less suitable. The natural frequency of the container wall, e.g. the closure, preferably lies within the range from 1/10 to 10 times the expected signal of the secondary oscillations, for example between 2 and 12 kHz in the case of beverage bottles.

Within the container, the cap signal is propagated at the sound velocity of the gas in the head space or at the sound velocity of the liquid. The junctions between liquid and gas and between liquid and container material each reflect the sound waves, so that standing waves can form as secondary oscillations within the container. Since the wavelength of the standing wave in the head space and that of the standing wave in the liquid depend upon the intervals of the phase transitions, if the composition of the gas in the head space is known the frequency of the secondary oscillation is a measure of the filling level within the container. Since the secondary oscillations within the container are excited and supplied with energy only by the original, primary cap oscillations, it is only after the decay of the highly damped cap signal that the standing waves become pronounced and detectable as a vibration signal, e.g. an acoustic signal, through the vibration of the side walls of the container, particularly the cap. It is thus possible for this signal also to be picked up by means of a vibration pick-up and for the filling level in the container to be determined through appropriate selection of a second measurement window.

In a first embodiment of the invention, therefore, the primary oscillation of the cap is differentiated from the standing waves or secondary oscillations within the head space of the container and within the volume of the liquid, which are excited by this oscillation, in that the second measurement window is located so that the primary oscillations of the cap have themselves essentially decayed and the picked-up oscillations signals consequently originate essentially from the standing waves or secondary oscillations.

If the two measurement windows cannot be sufficiently separated, the effective period of the primary cap oscillation continues to be influenced by the forming standing wave in the head space. However, if following expiry of the second measurement window, the frequency of the standing wave, as filling level information, and the frequency of the primary cap oscillation are known, the filling level information can also be used to compensate fully the impairment of the pressure information within the scope of the measuring accuracy. It is precisely in this connection that a further advantage of the time-differentiated analysis of a single signal becomes apparent, since there is no need for any adjustment between different sensors and thus the high accuracy is achieved with simple means.

Further information on parameters of a closed container can be obtained from the signals of the primary and secondary oscillations. The frequency of the secondary oscillation depends principally on the filling level, the temperature and the gas composition, e.g. the mixture ratio of two gases. If the filling level is measured in a conventional manner, e.g. through determination of weight or by means of a light barrier and if the temperature is known or constant, then the frequency of the secondary oscillation varies only with gas composition, for example with the mixture ratio of two gases. By means of the method according to the invention, therefore, with a known or constant temperature and a known filling level, it is possible to determine the sound velocity from the frequency and thus to determine the gas composition. The method can therefore also be used e.g. for determination of the $CO_2$ content of beverages containing carbon dioxide.

The method according to the invention thus enables information on the filling level, the internal pressure and the gas composition of a closed container to be selectively determined from the vibration signal with a low level of technical complexity. Since these items of information can be obtained independently of one another in respect of time, the individual items of information can also be acquired in combination.

In a second embodiment of the method according to the invention, the oscillations of the cap are not differentiated from the standing waves in the head space and within the volume of the liquid, or are not differentiated only through appropriate selection of the measurement window, but rather—in addition if necessary—both oscillations are differentiated by their frequency, through a frequency analysis (e.g. Fourier analysis). For example, the oscillation of the cap can be 7 kHz and the frequency of the standing waves 8 kHz. On the basis of the ascertained frequency of the standing waves in the head space of the container and within the volume of the liquid, and with a known gas composition, the filling level can be determined to an accuracy of 0.1 to 0.2 mm.

Sound waves are also propagated within the container material according to the same excitation principle, these sound waves being characteristic of the respective container. Variations from the standard frequency help to detect material defects. Due to the ratios of the oscillation amplitudes, the oscillation components of the container oscillation cannot be detected separately, but they can be unambiguously identified in the total spectrum following a frequency analysis.

In addition, it is possible to combine the new method with the analysis of the frequency spectrum of the already known method. Since the acquired individual items of information permit a precise assignment of the individual frequencies, they can be used for a better understanding and evaluation of the total spectrum, so that checking of the container material also becomes possible.

In fact, it is generally expedient to use both measurement windows and frequency analysis. The frequency spectrum obtained by means of Fourier analysis is generally relatively complex, since the signal form has several peaks. Since the time sequence of the oscillations cannot be read from the frequency spectrum, the oscillation frequencies sometimes cannot be uniquely assigned. In the case of containers of the same type, variations can occur independently between the internal pressures and, consequently, the cap tensions on the one hand and between the filling levels on the other hand, so that the situation can also occur whereby the primary oscillations and the secondary oscillations have the same frequency. However, the combination of the frequency analysis with the direct measurement of the frequency within measurement windows renders possible complete interpretation of the frequency analysis in each case. For this purpose, the position of the individual peaks can be determined in an automatic search process and matches with the individual results from the two measurement windows can be determined. The frequency peak which most closely matches the result value from the first measurement window corresponds to the pressure oscillation; the frequency peak which most closely matches the result value from the second measurement window corresponds to the filling level value. The result of the comparison can be substantiated in that further peaks relating to the filling level value exist in the spectrum which are in the ratio to one another of 1/2 to 2/2 to 3/2. Like secondary frequencies do not exist for the pressure oscillation. Following successful assignment in this manner, there is generally a single prominent peak remaining in the spectrum. This corresponds to the oscillation in the container material.

It is known that the sought measured values depend on several parameters. Thus, for example, in the case of completely intact containers the temperature of the content also determines to a large degree the internal pressure. Interruptions of a normally constant filling process can therefore result in temperature fluctuations and, consequently, in displacement of the measured values. In a real measurement installation, therefore, it may be necessary to make provisions to compensate temperature-related displacements. The method according to the invention is thus designed to pick up temperature information items by means of additional sensors and to compensate fully the displacement of measured values.

The processing of acoustic signals can be impaired by interference if the measurement apparatus is required to operate in environments with a high noise level. The signal-to-noise ratio can be improved by means of active and passive measures in order significantly to reduce these potential interferences. In addition to a noise-damping casing of the apparatus, the method according to the invention also makes provision whereby the actual measuring microphone is supplemented by an appropriate number of additional, appropriately located microphones. For example it is possible, in a simple configuration, to insert a second microphone which is oriented in the opposite direction. The subtraction of the ambient noises from the measured signal can accentuate the useful signal. In a more complex installation, several microphones are disposed in a circle the plane of which is perpendicular to the central axis of the examined container and the centre point of which lies exactly on the central axis of the examined container. This arrangement offers the advantage that the useful signal is picked up in phase balance by all microphones, whereas all interfering noises are picked up out of phase balance by the different microphones. A simple addition of the individual microphone signals thus improves the signal-to-noise ratio.

The individual items of information and the combined items of information on filling level, internal pressure and container condition can be evaluated in respect of various aspects. Firstly, a direct comparison of the respective individual items of information with predefined limiting values permits a clear identification of improperly filled, non-tight or damaged containers. Secondly, a statistical evaluation over the entire production or over selectable sections of the production can reflect the quality of the checked containers. Analysis of the mean values of the individual distributions offers the possibility of comparing the actual filling volumes and the achieved container pressures with the production specifications and, if necessary, of controlling the production process accordingly. The spread of the individual distributions reflects the constancy of the production process and its evaluation permits qualitative evaluation of the overall process, preventive maintenance and optimisation of the production cycle.

Continuous statistical evaluation also allows the possibility of linking the evaluation of the individual containers to the instantaneous position of the production mean value and evaluating the measured value deviations in relation to the statistical standard deviation. Statistical monitoring thus renders possible sensitive tracking of the limiting values and, consequently, good detection of defective containers even under changing production conditions.

BRIEF DESCRIPTION OF THE DRAWING

An embodiment example of the invention is described more fully below with reference to the drawing, wherein:

FIG. 2 shows a diagram of the signal amplitude over time, and

FIG. 3 shows a diagram of a frequency analysis.

DETAILED DESCRIPTION OF THE INVENTION

Figure 1:
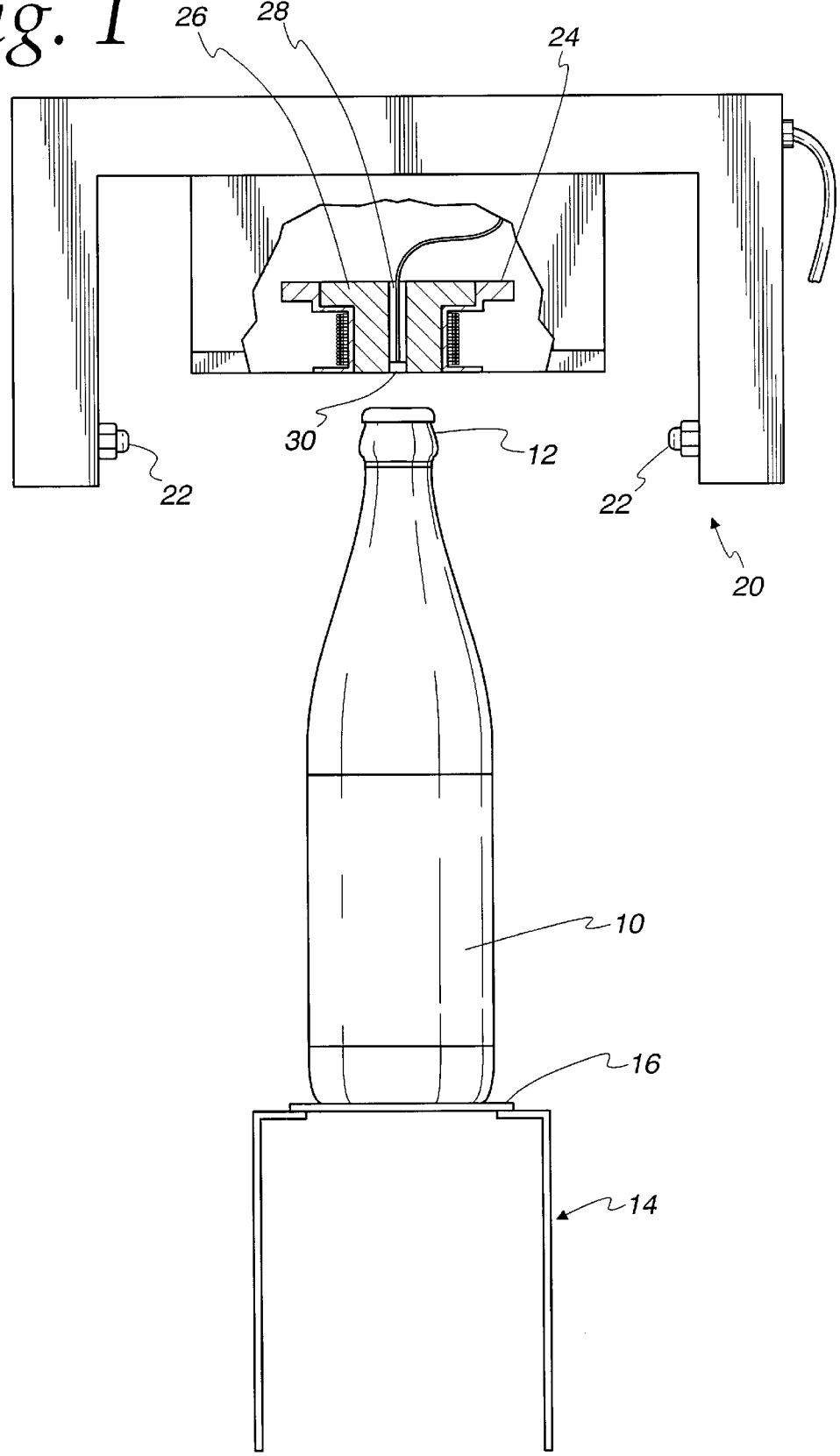
FIG. 1 shows in cross section a device for the determination of the filling level of liquids in containers which are closed by a cap.

In the case of the embodiment example depicted in FIG. 1, the liquid container is a normal 0.5 l beer bottle 10 with a crown cap closure 12. The bottle 10, standing on a transporter 14, is transported under and through a measuring system 20 by means of a link chain 16.

The measuring system 20 comprises a light barrier 22 the light beam of which strikes the bottle 10 immediately below the opening which is closed by the crown cap closure 12. Disposed at a distance of 3 to 10 mm above the crown cap closure 12 is a magnet coil 24 the axis of which runs vertically and therefore parallel to the longitudinal axis of the bottle 10. The magnet coil 24 comprises a core 26 with an axial bore 28 at the lower end of which there is disposed a microphone 30.

The height of the light barrier 22 above the transporter 14 and, likewise, the vertical distance between the light barrier 22 and both the magnet coil 24 and the microphone 30 can be varied, so that bottles of different sizes and shapes and also other containers can be examined.

In operation, the light barrier 22 generates a trigger signal at the instant at which the crown cap closure 12 is located under the magnet coil 24 and this trigger signal excites the magnet coil 24 by means of a short current pulse. The short-time magnetic field which is generated as a result briefly exerts on the metal crown cap closure 12 an upwardly directed force which initiates a primary mechanical oscillation or vibration in the crown cap closure 12. This vibration typically has a frequency of 7 kHz and can therefore be picked up by the microphone 30 as a acoustic signal.

The primary oscillation of the crown cap closure 12 is highly damped and decays within approximately 2 ms. At the same time, the primary oscillation of the crown cap closure 12 excites a standing acoustic wave within the air or gas column between the crown cap closure 12 and the liquid present in the bottle 10 and within the liquid. These standing waves exist as secondary oscillations which are time-shifted in relation to the primary oscillations of the crown cap closure 12 and have a frequency of, for example, 8 kHz. They continue to exist after the primary oscillation of the crown cap closure 12 has decayed and can be picked up by means of the microphone 30, through the crown cap closure 12.

FIG. 2 shows the characteristic of the signal amplitude (relative units) over time, in milliseconds. Such a diagram can be used for a first evaluation process, in which the time interval between the primary and secondary oscillation modes can be exploited for the purpose discrimination, the acoustic signal picked up by the microphone 30 arising principally from the primary natural oscillation of the crown cap closure 12 within a first measurement window F1 of e.g. 0.3 to 0.7 ms after the magnetic pulse (=0 ms). The pressure prevailing within the bottle 10 can be determined from the measured frequency. Within a second measurement window F2 of e.g. 3 to 4.8 ms after the magnetic pulse, the acoustic signal picked up by the microphone 30 arises principally from the secondary oscillations which have formed within the bottle 10 as standing waves. The frequency of these standing waves characterises the filling level. For example, if a bottle 10 having a setpoint filling level corresponding to a 5 cm high air space between the surface of the liquid and the crown cap closure 12 has a frequency of 8 kHz, then in the case of a 0.5 cm under-filling, the frequency is 7.25 kHz.

FIG. 3 shows the result of a frequency analysis, which renders possible a second evaluation process, in which the whole acoustic signal picked up within a time period of e.g. 10 ms after the magnetic pulse is subjected to a Fourier analysis. In the case of the embodiment example of FIG. 3, the frequency spectrum has a peak P1 at 7.2 kHz which corresponds to the primary oscillation of the crown cap closure 12, and a second peak P2 at 6 kHz which corresponds to the secondary oscillation of the standing waves within the bottle 10, this frequency being dependent on the filling level. Further amplitude peaks can be ascertained for other frequencies. If the frequency of the peak P2 is denoted by $\lambda$, then for the frequencies $\lambda/3$ and $3\lambda/2$ there occur peaks P3 and P4 respectively, which arise from harmonics of the secondary oscillation. Also distinguishable is a peak P5 which is caused by oscillations of the container material. Cracks or discontinuities within the wall of the bottle 10 become apparent through a division of this frequency amplitude P5 on to amplitude peaks with several frequencies or through a displacement to another frequency or through a complete disappearance of the peak P5.

The actual electronic circuits used for the two evaluation processes are of conventional construction and are therefore not described.

The frequency of the oscillations is expediently determined through direct measurement of the duration of the oscillation periods in which the time interval is measured between a defined number of positive zero crossings, e.g. eight, of the signal by means of a clock signal of e.g. 8 MHz. The signals are expediently evaluated through comparison of the measured signal values with stored empirical values.

What is claimed is:

1. A method for the determination of parameters of containers which comprise a container wall including a closure and contain a liquid and a space between the closure and the liquid, comprising the steps of:

exciting primary mechanical oscillations in the container wall;

picking up secondary oscillations which are excited in the container by the primary mechanical oscillations of the container wall and which occur within the space between the closure and the liquid, wherein the secondary oscillations are picked up separately from the primary oscillations by only those oscillations being picked up which occur within a time measurement window within which the primary oscillations have already decayed;

analyzing the secondary oscillations picked up; and determining the parameters on the ascertained frequency of the secondary oscillations picked up.

2. The method according to claim 1, wherein the determined parameters include a filling level.

3. The method according to claim 1 further comprising the step of determining the frequency of the primary oscillations by analysis of their frequency spectrum.

4. The method according to claim 3, wherein the primary and secondary oscillations are picked up within different time measurement windows.

5. The method according to claim 1, further comprising the step of subjecting the picked-up oscillation signals to a frequency analysis and the primary and secondary oscillations are picked up within different measurement windows.

6. The method according to claim 1, wherein for the purpose of improving the useful signal/interference signal ratio, the signals are picked up by means of a microphone arrangement which accentuates the useful signal by subtraction of the ambient noises from the measured signal.

7. The method according to claim 6, wherein a circular microphone arrangement is used which accentuates the useful signal through phase-balanced addition of the individual signals.

8. The method according to claim 5, wherein information is obtained from each measurement window to compensate for mutual influence.

9. The method according to claim 2 further comprising the step of determining the frequency of the primary oscillations by analysis of their frequency spectrum.

10. A method for determining a filling level of containers comprising a container wall including a closure and containing a liquid and a space between the closure and the liquid, comprising the steps of:

exciting primary mechanical oscillations in the container wall;

picking up secondary oscillations which are excited in the container by the primary mechanical oscillations of the container wall and which occur within the space between the closure and the liquid, wherein the secondary oscillations are picked up separately from the primary oscillations by only those oscillations being picked up which occur within a time measurement window within which the primary oscillations have already decayed;

analyzing the secondary oscillations picked up; and determining the filling level from the ascertained frequency of the secondary oscillations.

* * * * *